United States Patent
Ishii et al.

(10) Patent No.: US 9,471,999 B2
(45) Date of Patent: Oct. 18, 2016

(54) MEDICAL IMAGE DIAGNOSTIC APPARATUS

(71) Applicant: Toshiba Medical Systems Corporation, Otawara-shi (JP)

(72) Inventors: Hideaki Ishii, Nasushiobara (JP); Satoshi Wakai, Nasushiobara (JP); Kazumasa Arakita, Nasushiobara (JP); Takuma Igarashi, Nasushiobara (JP); Yasuko Fujisawa, Nasushiobara (JP); Shigeo Kaminaga, Otawara (JP); Kenji Hirohata, Tokyo (JP); Junichiro Ooga, Tokyo (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 14/725,426

(22) Filed: May 29, 2015

(65) Prior Publication Data

US 2015/0262388 A1    Sep. 17, 2015

Related U.S. Application Data

(63) Continuation of application No. PCT/JP2013/082372, filed on Dec. 2, 2013.

(30) Foreign Application Priority Data

Nov. 30, 2012  (JP) .................................. 2012-263353
Dec. 2, 2013   (JP) .................................. 2013-249059

(51) Int. Cl.
  *G06K 9/00*     (2006.01)
  *G06T 11/00*    (2006.01)
  (Continued)

(52) U.S. Cl.
  CPC ............. *G06T 11/003* (2013.01); *A61B 6/465* (2013.01); *A61B 6/486* (2013.01); *A61B 6/504* (2013.01);
  (Continued)

(58) Field of Classification Search
  CPC .... A61B 6/504; A61B 6/503; A61B 6/5217; A61B 6/5247; G06T 2207/30101; G06T 2207/10081; G06T 2207/30048; G06T 7/0024

USPC ......................................................... 382/131
See application file for complete search history.

(56) References Cited

U.S. PATENT DOCUMENTS 8,135,452 B2 *  3/2012  Dougherty ............. A61B 5/055
                                                      600/407
8,970,578 B2 *  3/2015  Voros ............................ 345/419
(Continued)

FOREIGN PATENT DOCUMENTS

JP     2009-28515 A     2/2009
JP     2014-108198 A    6/2014
(Continued)

OTHER PUBLICATIONS

International Search Report issued Mar. 11, 2014 for PCT/JP2013/082372 filed on Dec. 2, 2013 with English Translation.
(Continued)

*Primary Examiner* — Ali Bayat
(74) *Attorney, Agent, or Firm* — Oblon, McClelland, Maier & Neustadt, L.L.P

(57) ABSTRACT

According to one embodiment, a medical image diagnostic apparatus includes a storage memory, processing circuitry, and a display. The storage memory stores data of a plurality of FFR distribution maps constituting a time series regarding a coronary artery, and data of a plurality of morphological images corresponding to the time series. The processing circuitry converts the plurality of FFR distribution maps into a plurality of corresponding color maps, respectively. The display displays a plurality of superposed images obtained by superposing the plurality of color maps and the plurality of morphological images respectively corresponding in phase to the plurality of color maps. The display restricts display targets for the plurality of color maps based on the plurality of FFR distribution maps or the plurality of morphological images.

12 Claims, 10 Drawing Sheets

(51) Int. Cl.
*A61B 6/00* (2006.01)
*G06T 7/00* (2006.01)

(52) U.S. Cl.
CPC .......... *A61B 6/5217* (2013.01); *G06T 7/0024* (2013.01); *G06T 11/001* (2013.01); *A61B 6/503* (2013.01); *G06T 2207/10081* (2013.01); *G06T 2207/10088* (2013.01); *G06T 2207/10104* (2013.01); *G06T 2207/10108* (2013.01); *G06T 2207/30048* (2013.01); *G06T 2207/30101* (2013.01)

(56) References Cited

U.S. PATENT DOCUMENTS

| | | | | |
|---|---|---|---|---|
| 2005/0187471 | A1* | 8/2005 | Kanayama | A61B 5/0091 600/437 |
| 2009/0010519 | A1 | 1/2009 | Wakai et al. | |
| 2010/0066756 | A1* | 3/2010 | Yang | A61B 6/481 345/593 |
| 2012/0041739 | A1 | 2/2012 | Taylor | |
| 2012/0071782 | A1* | 3/2012 | Patil | A61B 5/0538 600/547 |
| 2014/0142398 | A1* | 5/2014 | Patil | A61B 6/463 600/301 |
| 2014/0142422 | A1* | 5/2014 | Manzke | A61B 19/5244 600/424 |
| 2014/0219524 | A1* | 8/2014 | Takeguchi | A61B 6/463 382/128 |

FOREIGN PATENT DOCUMENTS

| | | |
|---|---|---|
| JP | 2014-108199 A | 6/2014 |
| JP | 2014-108208 A | 6/2014 |
| JP | 2014-113264 A | 6/2014 |
| JP | 2014-128650 A | 7/2014 |
| WO | WO 2012/021307 A2 | 2/2012 |
| WO | WO 2014/027692 A1 | 2/2014 |

OTHER PUBLICATIONS

Written Opinion issued Mar. 11, 2014 for PCT/JP2013/082372 filed on Dec. 2, 2013.

* cited by examiner

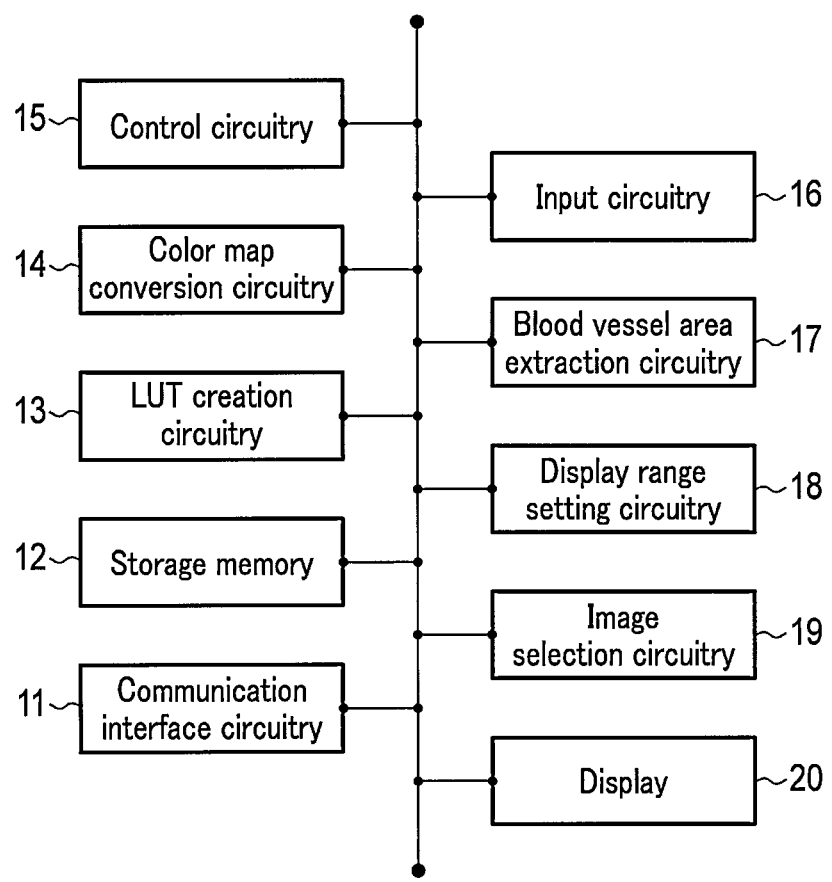
F I G. 1

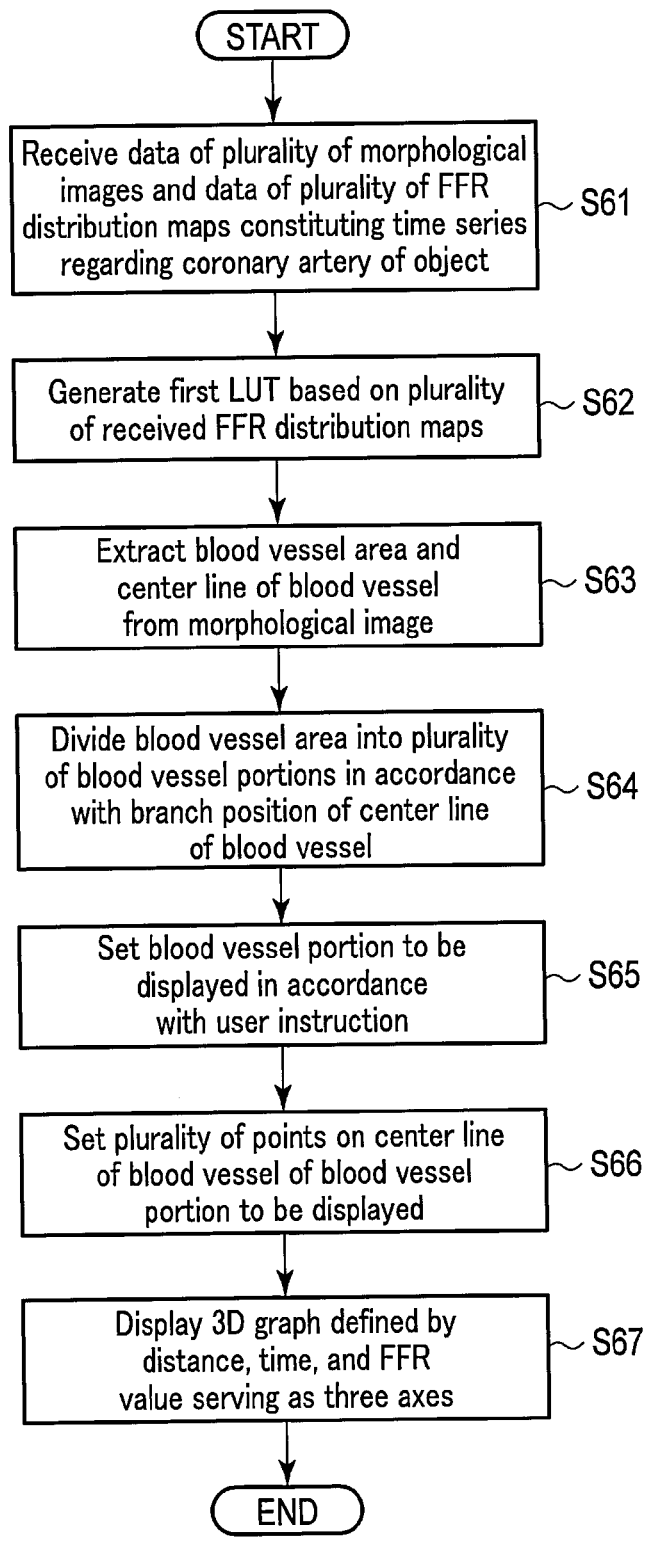
F I G. 7

MEDICAL IMAGE DIAGNOSTIC APPARATUS

CROSS-REFERENCE TO RELATED APPLICATIONS

This application is a Continuation Application of PCT Application No. PCT/JP2013/082372, filed Dec. 2, 2013 and based upon and claims the benefit of priority from prior Japanese Patent Application No. 2012-263353, filed Nov. 30, 2012 and Japanese Patent Application No. 2013-249059, filed Dec. 2, 2013, the entire contents of which are incorporated herein by reference.

FIELD

Embodiments described herein relate generally to a medical image diagnostic apparatus.

BACKGROUND

Recently, a Fractional Flow Reserve (FFR) analysis technique using a Computed Tomography (CT) apparatus has been developed. This technique generates a coronary artery shape model from CT volume data regarding a coronary artery that is collected by the CT apparatus, simulates a blood flow, and calculates a pressure value in the coronary artery. Information useful for angiostenosis treatment, such as FFR, can be noninvasively obtained based on the pressure value in the coronary artery. At present, the FFR analysis technique is applicable to a temporal change of the FFR result considering the heart beats of the coronary artery.

However, the heart beats at a short time interval, so the FFR value changes quickly on a display regarding a temporal change of the FFR result of the coronary artery. For this reason, an FFR value which should be noted, and the position of the FFR value may be missed.

BRIEF DESCRIPTION OF THE DRAWINGS

FIG. 1 is a block diagram showing an example of the arrangement of a medical image diagnostic apparatus according to an embodiment.

FIG. 7 is a flowchart showing processing procedures in the blood vessel display mode of the medical image diagnostic apparatus according to this embodiment.

DETAILED DESCRIPTION

Figure 2:
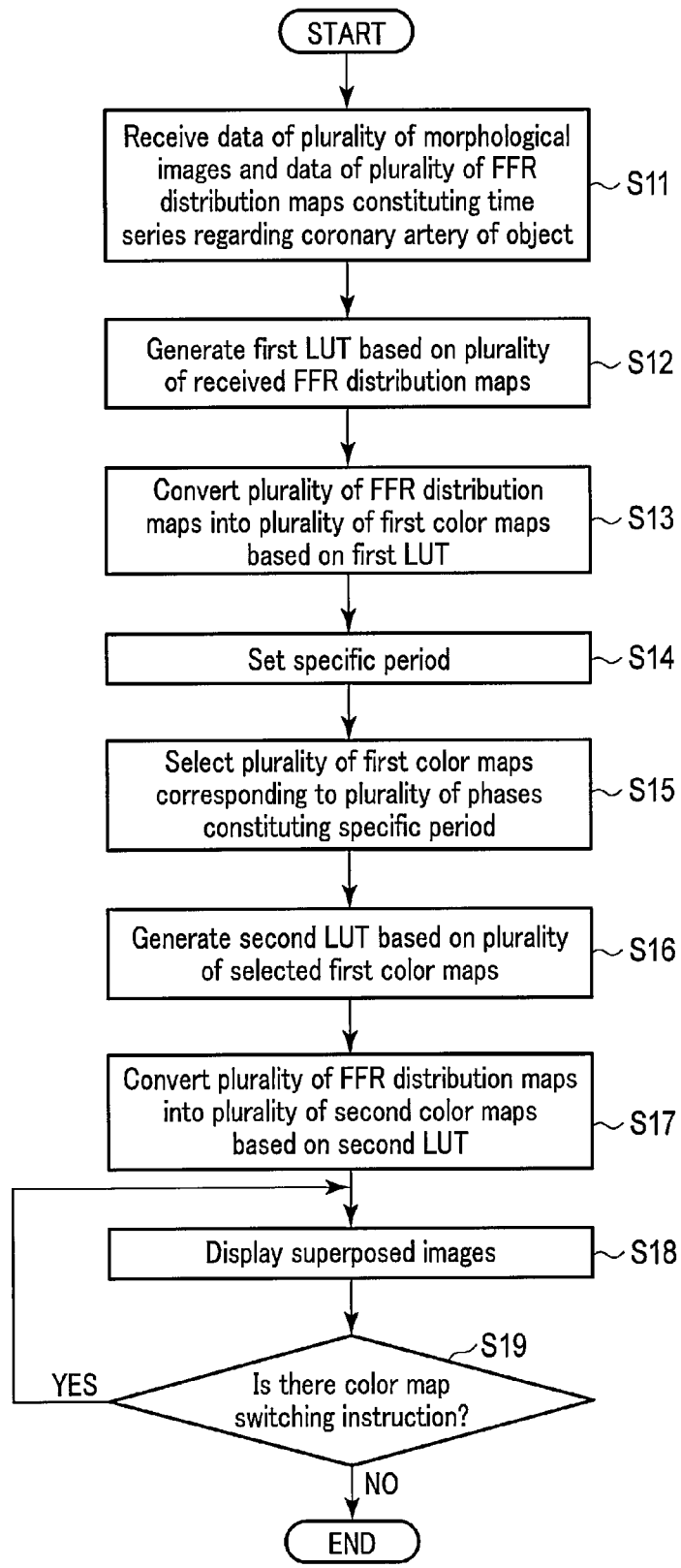
FIG. 2 is a flowchart showing processing procedures in the specific period display mode of a medical image diagnostic apparatus 1 according to this embodiment.

In general, according to one embodiment, a medical image diagnostic apparatus includes a storage memory, processing circuitry, and a display. The storage memory stores data of a plurality of Fractional Flow Reserve (FFR) distribution maps constituting a time series regarding a coronary artery, and data of a plurality of morphological images corresponding to the time series. The processing circuitry converts the plurality of FFR distribution maps into a plurality of corresponding color maps, respectively. The display displays a plurality of superposed images obtained by superposing the plurality of color maps and the plurality of morphological images respectively corresponding in phase to the plurality of color maps. The display restricts display targets for the plurality of color maps based on the plurality of FFR distribution maps or the plurality of morphological images.

A medical image diagnostic apparatus according to an embodiment will now be described with reference to the accompanying drawings. In the following description, the same reference numerals denote parts having almost the same functions and arrangements, and a repetitive description is made only if necessary.

FIG. 1 is a block diagram showing an example of the arrangement of a medical image diagnostic apparatus 1 according to this embodiment. As shown in FIG. 1, the medical image diagnostic apparatus 1 includes a communication interface circuitry 11, a storage memory 12, an LUT generation circuitry 13 (correspondence table generation circuitry 13), a color map conversion circuitry 14, a control circuitry 15, an input circuitry 16, a blood vessel area extraction circuitry 17, a display range setting circuitry 18, an image selection circuitry 19, and a display 20.

The medical image diagnostic apparatus 1 according to this embodiment is connected to external apparatuses such as a CT (Computed Tomography) apparatus, a medical image processing apparatus, and a PACS (Picture Archiving and Communication System) via networks such as a LAN (Local Area Network) and a public electronic communication network. The medical image diagnostic apparatus 1 includes the communication interface circuitry 11 for connecting to an external apparatus via a network. The communication interface circuitry 11 includes, for example, a connector circuitry (not shown) for connecting the medical image diagnostic apparatus 1 to an external apparatus or the like via a cable or the like, and a wireless signal reception circuitry (not shown) for receiving a wireless signal from an external apparatus. The medical image diagnostic apparatus 1 transmits/receives data to/from an external apparatus via the communication interface circuitry 11 under the control of the control circuitry 15 (to be described later).

The storage memory 12 includes, for example, a semiconductor storage device such as a Flash SSD (Solid State Disk) serving as a semiconductor storage element, and an HDD (Hard Disk Drive). Under the control of the control circuitry 15, the storage memory 12 stores data of a plurality of types of images transmitted from external apparatuses. A plurality of images include a plurality of morphological images (to be simply referred to as a plurality of morphological images hereinafter), a plurality of FFR (Fractional Flow Reserve) distribution maps (to be simply referred to as a plurality of FFR distribution maps hereinafter), and a plurality of myocardial perfusion images regarding a cardiac muscle to which the coronary artery of an object supplies blood. A plurality of medical images of these types each constitute a time series regarding the coronary artery of an object. Note that a myocardial perfusion image may be an image generated not only by a CT apparatus but also by another modality such as an MRI apparatus. Note that the above-mentioned images handled in the medical image diagnostic apparatus 1 are 3D image data, unless otherwise specified. A morphological image includes a 3D coronary artery model. A time series regarding the coronary artery of an object includes at least a plurality of phases in one cycle of heart beats of the object. A plurality of phases regarding a morphological image include at least a plurality of phases regarding an FFR distribution map. The range of an object including a coronary artery in a morphological image includes at least the range of the object including the coronary artery in an FFR distribution map.

The storage memory 12 stores data of an LUT (Look Up Table) generated by the LUT generation circuitry 13 (to be described later). The LUT is a table that associates pieces of color information with a plurality of FFR values, respectively. The color information includes, for example, the type of color, the density of the color, and the fill effect of the color. Note that the storage memory 12 may store data of an LUT that associates in advance pieces of color information with a plurality of FFR values, respectively. At this time, the minimum value of the FFR value is 0 and its maximum value is 1 in the LUT stored in advance in the storage memory 12.

Also, the storage memory 12 stores data regarding detailed conditions of a display mode (to be described later) input by a user via the input circuitry 16. Note that the storage memory 12 may hold, without change, data of the aforementioned plurality of types of medical images that have been received via the communication interface circuitry 11 and stored, or the data may be erased in response to the end of a user operation to the medical image diagnostic apparatus 1.

The LUT generation circuitry 13 is processing circuitry that generates an LUT based on a master table and data of an LUT generation target. The LUT generation circuitry 13 reads a program corresponding to a LUT generation function from storage memory 12, and executes the program to realize the LUT generation function. The master table is a table that associates, for example, 10 pieces of color information respectively with 10 FFR values obtained by division into 10 equal parts from a minimum value to a maximum value. The equal division count, the color information assignment order, the number of pieces of color information, and the like can be properly changed in accordance with user instructions via the input circuitry 16. First, the LUT generation circuitry 13 specifies the minimum and maximum values of the FFR value from data of an LUT generation target. The LUT generation target includes, for example, 1) data of a plurality of FFR distribution maps, 2) data of ranges respectively set from a plurality of color maps or a plurality of morphological images by the display range setting circuitry 18, and 3) data of a plurality of color maps extracted from a plurality of color maps by the image selection unit 19 (to be described later). The interval between the minimum and maximum values of the FFR value is equally divided by the division count of a value in the master table. Then, the LUT generation circuitry 13 adds pieces of color information defined in the master table to the minimum value of the FFR value, the maximum value of the FFR value, and the plurality of FFR values obtained by equally dividing the interval, respectively, thereby generating an LUT.

The color map conversion circuitry 14 is processing circuitry that converts a graph regarding the FFR value into a color graph to which color information is added based on the LUT. The color map conversion circuitry 14 reads a program corresponding to a color map conversion function from storage memory 12, and executes the program to realize the color map conversion function.

The control circuitry 15 is processing circuitry that controls the respective circuitry of the medical image diagnostic apparatus 1 based on input information received from the input circuitry 16. The control circuitry 15 reads a program corresponding to a control function from storage memory 12, and executes the program to realize the control function. The input information input from the input unit 16 is temporarily stored in a memory circuit included in the control circuitry 15.

The input circuitry 16 functions as an interface for accepting instruction information from the user to the medical image diagnostic apparatus 1. As the input circuitry 16, input devices such as a mouse, keyboard, trackball, touch panel, and button are properly usable.

More specifically, the input circuitry 16 accepts an input of a display mode for the FFR result of a coronary artery by the user. The FFR result of a coronary artery represents a temporal change of the FFR regarding the blood vessel area of the coronary artery in one cycle of heart beats. Display modes for the FFR result of the coronary artery include a specific period display mode, a thinning display mode, a local display mode, a blood vessel display mode, and an FFR value-limited mode. These display modes are display modes provided by the medical image diagnostic apparatus 1 in order to improve the image interpretation efficiency of the FFR result of a coronary artery by the user. The input circuitry 16 accepts an input of detailed conditions in each mode by the user. Each mode and its detailed conditions will be described later.

The input circuitry 16 also accepts an input of a display target for a plurality of color maps on the display 20.

For example, the input circuitry 16 accepts an input of the range of the above-mentioned display target by a user operation on a morphological image or an FFR distribution map. For example, the user can input the range of the above-mentioned display target by designating a range where he wants to check a temporal change of the FFR value by a mouse operation on a morphological image or an FFR distribution map. At this time, the user may designate the range of the target for each image. Alternatively, the user may designate the range of the target on a representative image out of a plurality of morphological images or a plurality of FFR distribution maps, and the range designated on the representative image may be applied to other images.

Instead, the display 20 may display electrocardiographic waveforms (or electrocardiographic waveform models) corresponding to a plurality of morphological images, and the FFR distribution map of the above-mentioned display target may be designated by a user operation on the displayed electrocardiographic waveform.

In addition, the input circuitry 16 accepts an input for setting ranges (to be referred to as color display ranges hereinafter) to be displayed in color on the display 20 from a plurality of color maps, respectively. For example, when the display range setting circuitry 18 sets a color display range based on the FFR value, the user can set an FFR value range by inputting at least one of the upper and lower limit values of an FFR value to be displayed. For example, the user sets an FFR value of 0.8 or less, and can set a color display range where it can be estimated that angiostenosis is severe.

Further, the input circuitry 16 accepts display/non-display user instructions regarding a myocardial perfusion image and polar map to the display 20 (to be described later). The input circuitry 16 accepts a switching operation of each display mode described above and a switching operation between setting and cancellation of each display mode.

The blood vessel area extraction circuitry 17 is processing circuitry. The processing circuitry reads a program corresponding to a function of the blood vessel area extraction circuitry 17, and executes the program to realize the function of the blood vessel area extraction circuitry 17. The blood vessel area extraction circuitry 17 extracts a blood vessel area from a morphological image based on a luminance value. Then, the blood vessel area extraction circuitry 17 specifies, from the extracted blood vessel area, at least one of an angiostenosis position, a blood vessel branch position, the position of a blood vessel having a predetermined width or more, and the position of a blood vessel having a predetermined width or less. The angiostenosis position can be specified according to, for example, the change amount of the inside diameter value of an extracted blood vessel area. This is because the inside diameter value of a blood vessel does not greatly vary in a range other than a branch position and the end of a blood vessel in a coronary artery, and a range having a large change amount of the inside diameter value is highly likely to be a stenosis range. As for the blood vessel branch position, for example, a center line is specified from an extracted blood vessel area, and the blood vessel branch position can be specified from a position where the center line branches. The position of a blood vessel having a predetermined width or more, or a predetermined width or less can be specified based on supplementary information, imaging conditions, or the like.

The display range setting circuitry 18 is processing circuitry. The processing circuitry reads a program corresponding to a function of the display range setting circuitry 18, and executes the program to realize the function of the display range setting circuitry 18. The display range setting circuitry 18 sets display targets from a plurality of color maps, respectively, based on the FFR value (in the FFR value-limited mode to be described later). The display range setting circuitry 18 sets display targets from a plurality of color maps, respectively, based on an angiostenosis position, a blood vessel branch position, and the position of a blood vessel having a predetermined width or more, which have been extracted from a plurality of morphological images by the blood vessel area extraction circuitry 17 (in the local display mode to be described later). A display range setting method by the display range setting circuitry 18 will be described later.

The image selection circuitry 19 is processing circuitry that extracts the color map of a display target from a plurality of color maps based on the heart beat phase (specific period display mode to be described later). The image selection circuitry 19 reads a program corresponding to an image selection function from storage memory 12, and executes the program to realize the image selection function. An image selection method by the image selection circuitry 19 will be described later.

The display 20 displays a plurality of superposed images obtained by superposing a plurality of color maps and a plurality of morphological images corresponding in phase to the plurality of color maps. In the specific period mode and the thinning mode (to be described later), the color map of a display target is a color map extracted by the image selection circuitry 19. In the local display mode and the FFR value-limited mode (to be described later), the color map of a display target includes all color maps. However, in each of a plurality of color maps, only a color display range is displayed in color. In each mode, therefore, the display 20 displays a superposed image in which the display targets for a plurality of color maps are restricted. The display 20 may display a plurality of superimposed images obtained by superimposing a plurality of color maps and a plurality of morphological images corresponding in phase to the plurality of color maps.

The display 20 displays soft buttons and the like for accepting, from the user, a display mode switching operation and an operation to switch an LUT used for color map generation.

Next, the specific period display mode provided by the medical image diagnostic apparatus 1 according to this embodiment will be explained.

(Specific Period Display Mode)

The specific period display mode is a mode in which a temporal change of a superposed image in a specific period of one cycle of heart beats of an object is displayed.

FIG. 2 is a flowchart showing processing procedures in the specific period display mode of the medical image diagnostic apparatus 1 according to this embodiment. First, data of a plurality of morphological images and data of a plurality of FFR distribution maps regarding the coronary artery of an object are received from external apparatuses via the communication interface circuitry 11 (step S11). The LUT generation circuitry 13 generates the first LUT based on the plurality of received FFR distribution maps (step S12).

Based on the first LUT, the color map conversion circuitry 14 converts the plurality of FFR distribution maps into a plurality of corresponding first color maps, respectively (step S13).

Then, a specific period is set (step S14). Specific periods are, for example, the diastolic period of the heart, the systolic period of the heart, and a period designated by a user (to be referred to as a user-designated period hereinafter). The user-designated period can be set by, for example, designating a display start phase and a display end phase by the user on the moving image of a morphological image that changes over time. The diastolic period and systolic period of the heart can be specified based on, for example, information equivalent to the phase of an electrocardiographic waveform added to each morphological image.

The image selection circuitry 19 selects a plurality of first color maps corresponding to a plurality of phases constituting the specific period from the plurality of first color maps converted in step S13 (step S15).

The LUT generation circuitry 13 generates the second LUT based on FFR values included in the plurality of first color maps corresponding to the plurality of phases constituting the specific period (step S16).

Based on the second LUT, the color map conversion circuitry 14 converts the plurality of FFR distribution maps into a plurality of corresponding second color maps, respectively (step S17).

The display 20 displays a plurality of superposed images obtained by superposing the plurality of color maps corresponding to the plurality of phases constituting the specific period, and a plurality of morphological images respectively corresponding to the plurality of color maps (step S18). At this time, the plurality of color maps corresponding to the plurality of phases constituting the specific period correspond to the plurality of first color maps or the plurality of second color maps. For example, when a color map used for a displayed superposed image is the first color map, if the user gives an instruction to switch the color map in step S19, the display 20 switches the color map used for a superposed image from the first color map to the second color map.

Every time the user gives a color map switching instruction, the respective circuitry repetitively execute the processing in step S18 (step S19).

Next, the thinning display mode provided by the medical image diagnostic apparatus 1 according to this embodiment will be explained.

(Thinning Display Mode)

The thinning display mode is a mode in which temporal changes of a plurality of superposed images left after thinning processing on a plurality of superposed images corresponding to a plurality of phases constituting one cycle of heart beats of an object are displayed.

Figure 3:
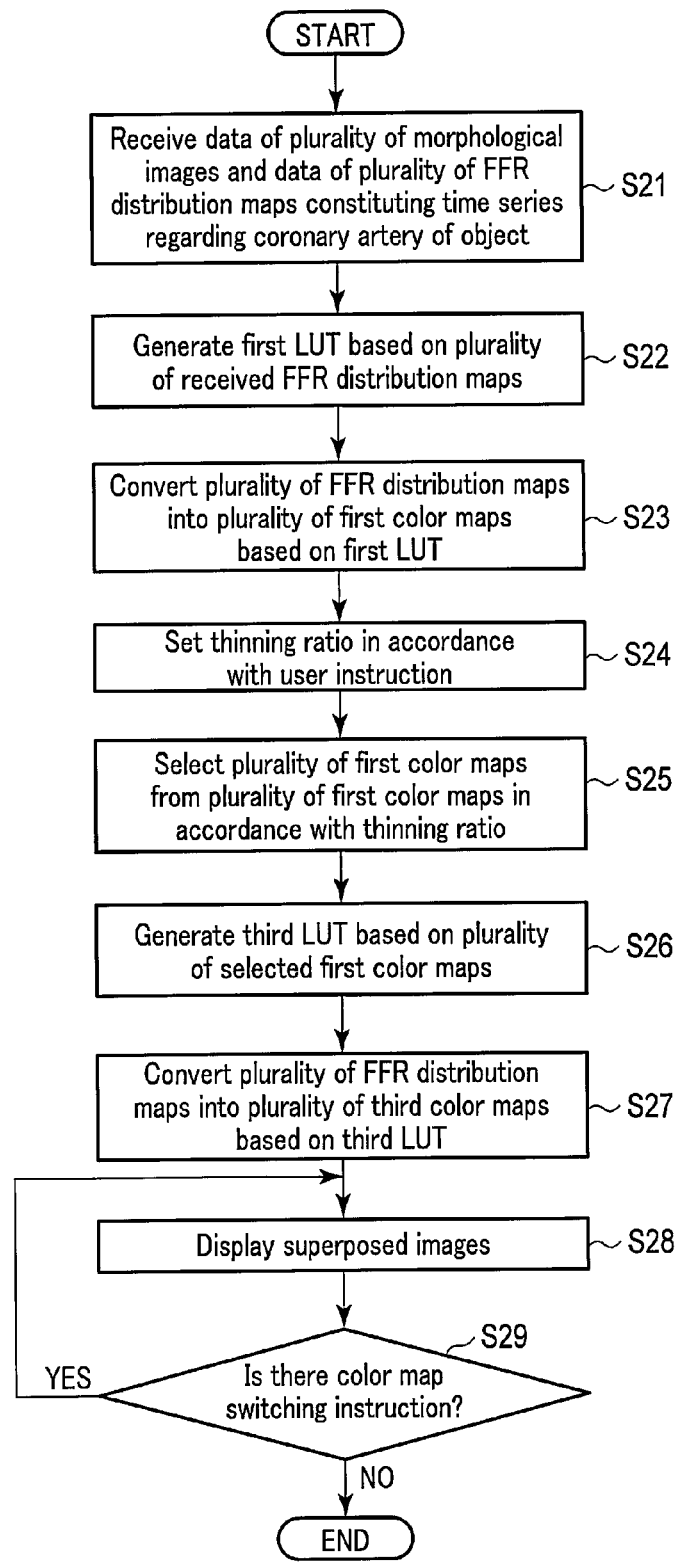
FIG. 3 is a flowchart showing processing procedures in the thinning display mode of the medical image diagnostic apparatus according to this embodiment.

FIG. 3 is a flowchart showing processing procedures in the thinning display mode of the medical image diagnostic apparatus 1 according to this embodiment. First, data of a plurality of morphological images and data of a plurality of FFR distribution maps regarding the coronary artery of an object are received from external apparatuses via the communication interface circuitry 11 (step S21). The LUT generation circuitry 13 generates the first LUT based on the plurality of received FFR distribution maps (step S22).

Based on the first LUT, the color map conversion circuitry 14 converts the plurality of FFR distribution maps into a plurality of corresponding first color maps, respectively (step S23).

The thinning ratio is set in accordance with a user instruction via the input circuitry 16 (step S24). The image selection circuitry 19 selects a plurality of first color maps from the plurality of first color maps in accordance with the thinning ratio set in step S24 (step S25). The LUT generation circuitry 13 generates the third LUT based on FFR values included in the first color maps selected in step S25 (step S26).

Based on the third LUT, the color map conversion circuitry 14 converts the plurality of FFR distribution maps into a plurality of corresponding third color maps, respectively (step S27).

The display 20 displays a plurality of superposed images obtained by superposing the plurality of color maps selected from the plurality of color maps in accordance with the thinning ratio set in step S24, and a plurality of morphological images respectively corresponding to the plurality of selected color maps (step S28). At this time, the plurality of color maps correspond to the plurality of first color maps or the plurality of third color maps. For example, when a color map used for a displayed superposed image is the first color map, if the user gives an instruction to switch the color map in step S29, the display 20 switches the color map used for a superposed image from the first color map to the third color map.

Every time the user gives a color map switching instruction, the respective circuitry repetitively execute the processing in step S28 (step S29).

Next, the local display mode provided by the medical image diagnostic apparatus 1 according to this embodiment will be explained.

(Local Display Mode)

The local display mode is a mode in which a temporal change of a superposed image in a specific range in the coronary artery of an object is displayed.

Figure 4:
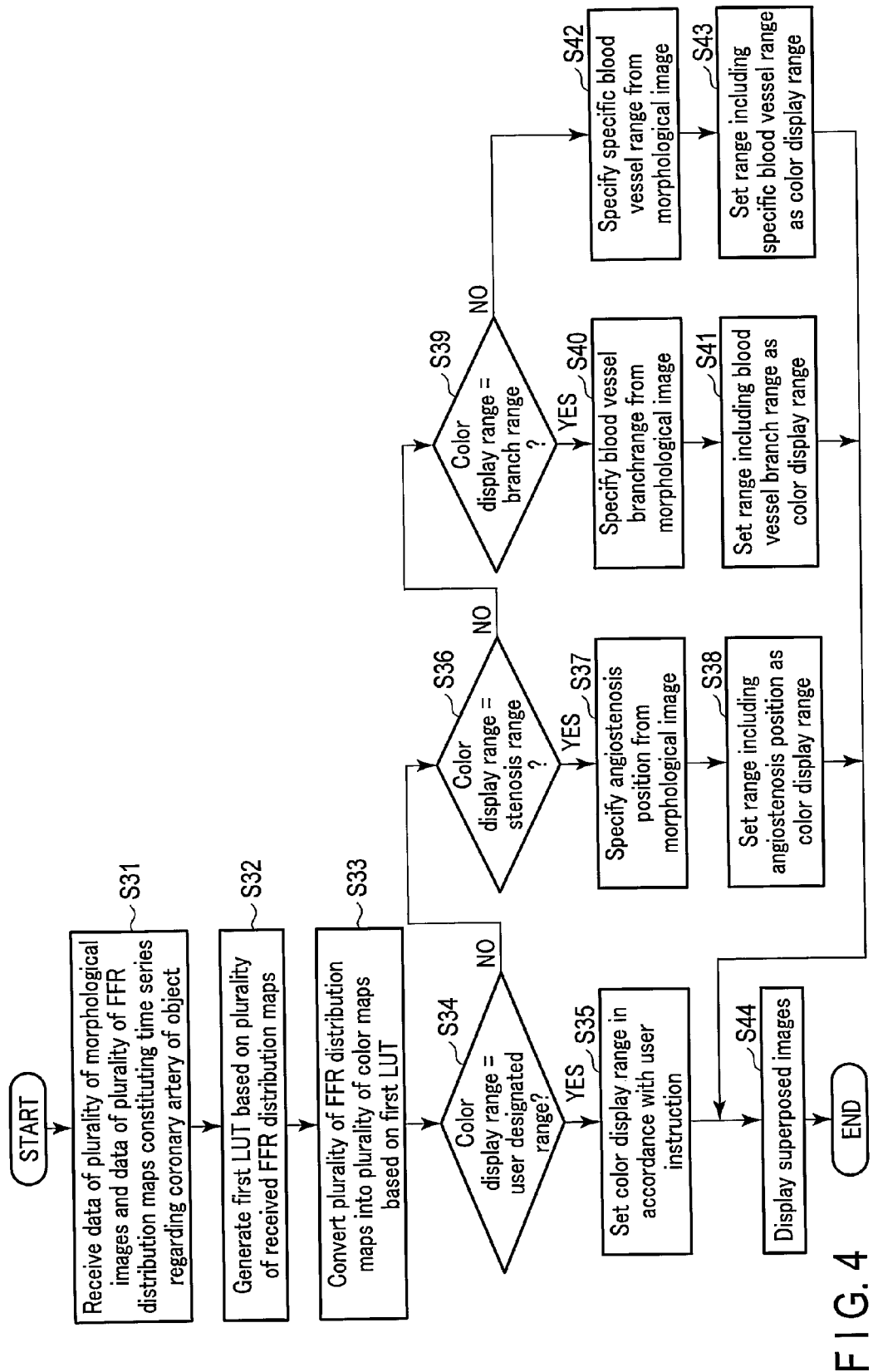
FIG. 4 is a flowchart showing processing procedures in the local display mode of the medical image diagnostic apparatus according to this embodiment.

FIG. 4 is a flowchart showing processing procedures in the local display mode of the medical image diagnostic apparatus 1 according to this embodiment. First, data of a plurality of morphological images and data of a plurality of FFR distribution maps regarding the coronary artery of an object are received from external apparatuses via the communication interface circuitry 11 (step S31). The LUT generation circuitry 13 generates the first LUT based on the plurality of received FFR distribution maps (step S32).

Based on the first LUT, the color map conversion circuitry 14 converts the plurality of FFR distribution maps into a plurality of corresponding color maps, respectively (step S33).

The type of a color display range is accepted via the input circuitry 16. More specifically, the user selects at least one display range from the following four types of display ranges. The four types of display ranges are, for example, a range designated by a user (to be referred to as a user-designated range hereinafter), a range including the stenosis site of a blood vessel (to be referred to as a stenosis range hereinafter), a range including the branch position of a blood vessel (to be referred to as a branch range hereinafter), and a range where the inside diameter of a blood vessel is equal to or larger than a specific width (to be referred to as a specific blood vessel range hereinafter).

If the "user-designated range" is selected as the color display range (step S34), the display range setting circuitry 18 sets, as the color display range, a range designated by the user on a morphological image or an FFR distribution map (step S35).

If the "stenosis range" is selected as the color display range (step S36), the blood vessel area extraction circuitry 17 extracts a blood vessel area from a morphological image. An angiostenosis position is specified from the extracted blood vessel area (step S37). The display range setting circuitry 18 sets, as the color display range, a range obtained by adding a predetermined margin in each of four directions from the angiostenosis position (step S38). Note that the predetermined margin is stored in advance in the storage memory 12 and can be properly changed in accordance with a user instruction via the input circuitry 16.

If the "branch range" is selected as the color display range (step S39), the blood vessel area extraction circuitry 17 extracts a blood vessel area from a morphological image. A blood vessel branch position is specified from the extracted blood vessel area (step S40). The display range setting circuitry 18 sets, as the display range, a range of a predetermined size using the blood vessel branch position as the center of the display (step S41). Note that the predetermined size is set to, for example, "a range of 5 cm from the blood vessel branch position", and data of this setting is stored in advance in the storage memory 12. Note that data of the setting can be properly changed in accordance with a user instruction via the input circuitry 16.

If the display method is none of the above-described methods, the color display range is a "specific blood vessel range". The blood vessel area extraction circuitry 17 extracts a blood vessel area from a morphological image. A specific blood vessel range is specified from the extracted blood vessel area (step S42). The specific blood vessel range is, for example, the range of a blood vessel area where the inside diameter is larger than a predetermined value, or the range of a blood vessel area where the inside diameter of a blood vessel is smaller than a predetermined value. The display range setting circuitry 18 sets, as the display range, a range obtained by adding a margin in each of four directions of a specific blood vessel range (step S43).

The display 20 sets the color display range as a display target, and displays superposed images obtained by superposing a plurality of color maps and a plurality of morphological images respectively corresponding in phase to the plurality of color maps (step S44).

In steps S17, S27, and S44, the display 20 may display superposed images obtained by position matching and phase matching of a plurality of morphological images and a plurality of color maps with respect to a plurality of myocardial perfusion images. Similarly, in steps S17, S27, and S44, the display 20 may display superposed images obtained by position matching and phase matching of a plurality of morphological images and a plurality of color maps with respect to a plurality of polar maps. Display/non-display of these images can be properly switched in accordance with a user instruction via the input circuitry 16.

Figure 5:
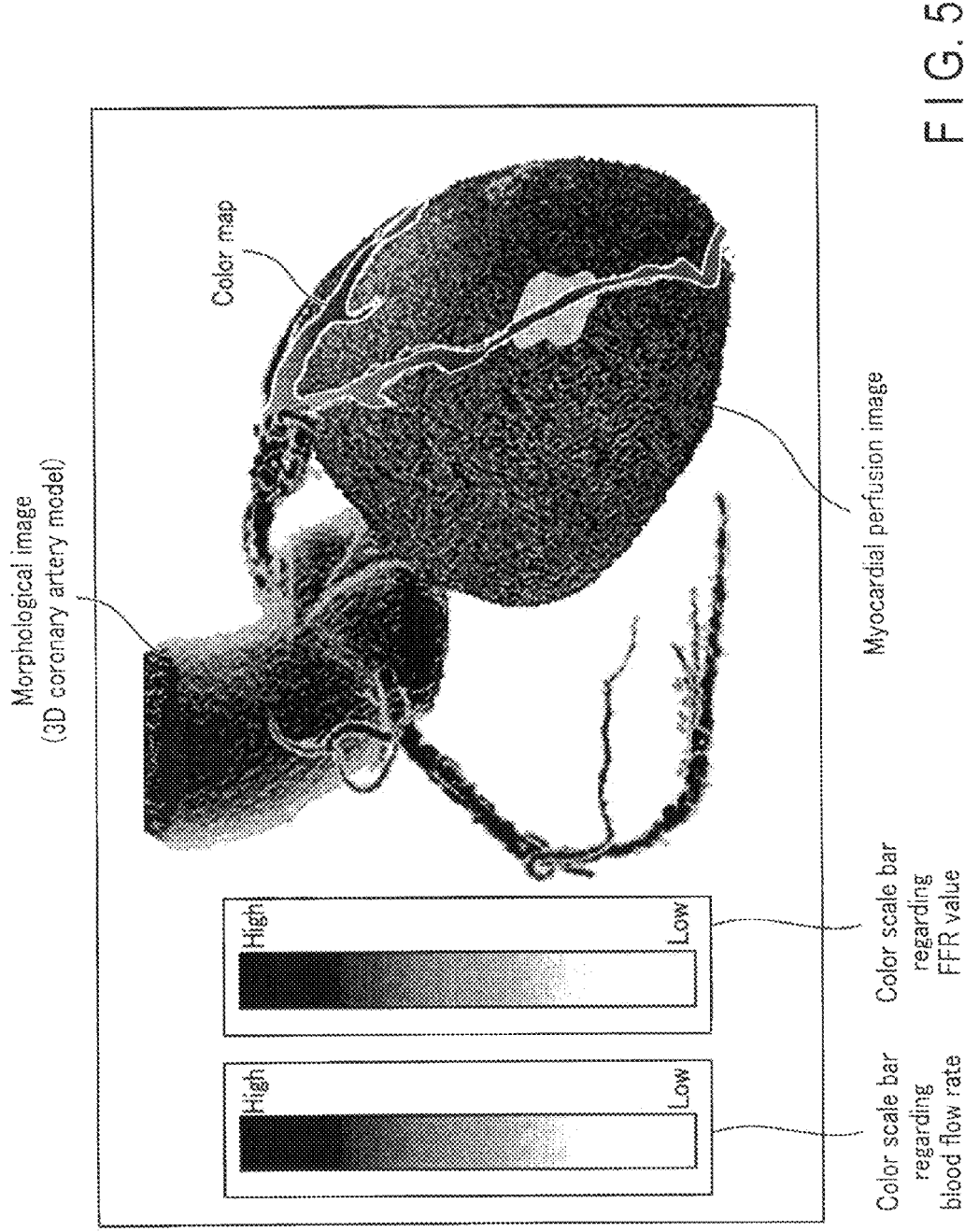
FIG. 5 is a view showing an example of display of a superposed image obtained by superposing a morphological image and a color map on a myocardial perfusion image.

FIG. 5 is a view showing an example of display of a superposed image obtained by superposing a morphological image and a color map on a myocardial perfusion image. As shown in FIG. 5, a superposed image obtained by superposing a morphological image (3D coronary artery model) and a color map on a myocardial perfusion image is displayed. As shown in FIG. 5, the partial range of the myocardial perfusion image may be displayed as the myocardial perfusion image. At this time, the displayed partial range can be set in accordance with a user instruction via the input circuitry 16. The display 20 may automatically display a superposed image so that the superposed image includes an ischemic area on the myocardial perfusion image. A color scale bar regarding the FFR value is displayed in accordance with an LUT used for conversion from an FFR distribution map into a color map, and represents the magnitude of the FFR value by color. A color scale bar regarding the blood flow rate is applied to the color display of a myocardial perfusion image, and represents the blood flow rate by color. In the display of FIG. 5, a functional image regarding a cardiac muscle to which a coronary artery supplies blood is displayed by position matching on a superposed image regarding the coronary artery. The user can interpret a temporal change of the FFR value of the coronary artery and a state change of the cardiac muscle together. This can improve the image interpretation efficiency and diagnosis accuracy by the user. Therefore, the myocardial perfusion image may be another image as long as it is a functional image representing the state of the cardiac muscle. Functional images may be functional images generated by, for example, functional image diagnosis using SPECT, delayed enhancement imaging using MRI, and functional image diagnosis using PET. A functional image representing the state of the cardiac muscle may be, for example, a polar map corresponding to a myocardial perfusion image. At this time, the functional image representing the state of the cardiac muscle may be stored in the storage memory 12 or stored in a PACS or the like connected via the communication interface circuitry 11.

Figure 6:
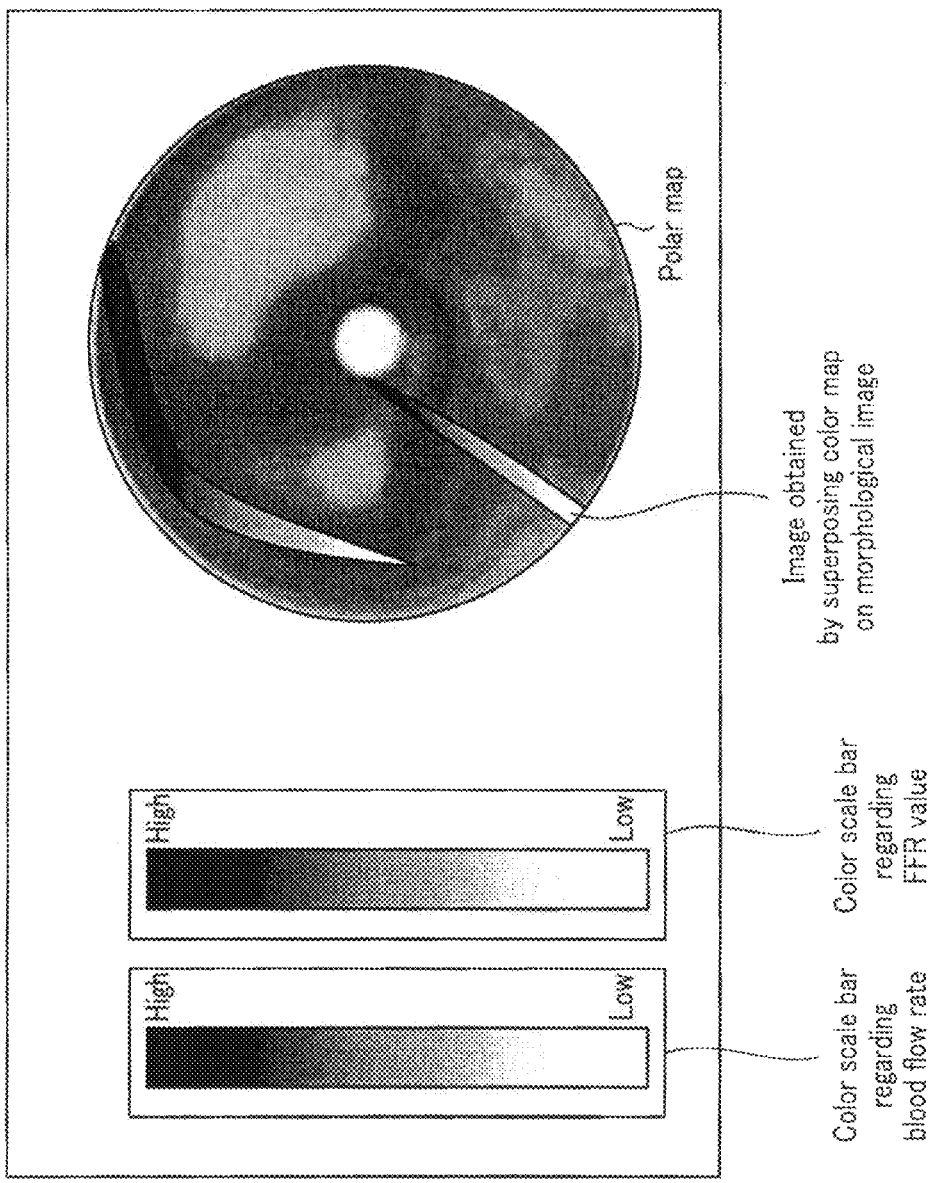
FIG. 6 is a view showing an example of display of a superposed image obtained by superposing a morphological image and a color map on a polar map.

FIG. 6 is a view showing an example of display of a superposed image obtained by superposing a morphological image and a color map on a polar map. At this time, assume that the storage memory 12 stores data of a plurality of polar maps corresponding to a plurality of myocardial perfusion images regarding a cardiac muscle to which the coronary artery of an object supplies blood. As shown in FIG. 6, a superposed image obtained by superposing a morphological image and a color map on a polar map is displayed. A color scale bar regarding the FFR value is displayed in accordance with an LUT used for conversion from an FFR distribution map into a color map, and represents the magnitude of the FFR value by color. A color scale bar regarding the blood flow rate is applied to the color display of a polar map, and represents the blood flow rate by color.

Next, the blood vessel display mode provided by the medical image diagnostic apparatus 1 according to this embodiment will be explained.

(Blood Vessel Display Mode)

The blood vessel display mode is a mode in which a temporal change of the FFR result of each blood vessel in the coronary artery of an object is displayed.

FIG. 7 is a flowchart showing processing procedures in the blood vessel display mode of the medical image diagnostic apparatus 1 according to this embodiment. First, data of a plurality of morphological images and data of a plurality of FFR distribution maps regarding the coronary artery of an object are received from external apparatuses via the communication interface circuitry 11 (step S61). The LUT generation circuitry 13 generates the first LUT based on the plurality of received FFR distribution maps (step S62).

The blood vessel area extraction circuitry 17 extracts a blood vessel area from a morphological image, and extracts the center line of a blood vessel from the extracted blood vessel area (step S63). Then, the branch position of the extracted center line of the blood vessel is specified. The extracted blood vessel area is divided into a plurality of blood vessel portions in accordance with the branch position of the center line of the blood vessel (step S64). A blood vessel portion to be displayed is set in accordance with a user instruction via the input circuitry 16 (step S65). The blood vessel portion can be set by, for example, a mouse operation by the user on a displayed morphological image. The blood vessel area extraction circuitry 17 sets a plurality of points along the center line of the blood vessel using, as a start point, a branch position on the center line of the blood vessel of the blood vessel portion to be displayed (step S66).

The display 20 displays a 3D graph defined by three axes that are the distance, the lapse of time, and the FFR value (step S67). The distance is a distance from a predetermined position of the blood vessel portion to be displayed, for example, from a blood vessel branch position to each of a plurality of points. The lapse of time is the lapse of time from a reference that is predetermined time of the time series. The predetermined time is, for example, the systolic end or diastolic end of the heart. The FFR value is the FFR value of a given point at given time.

Figure 8:
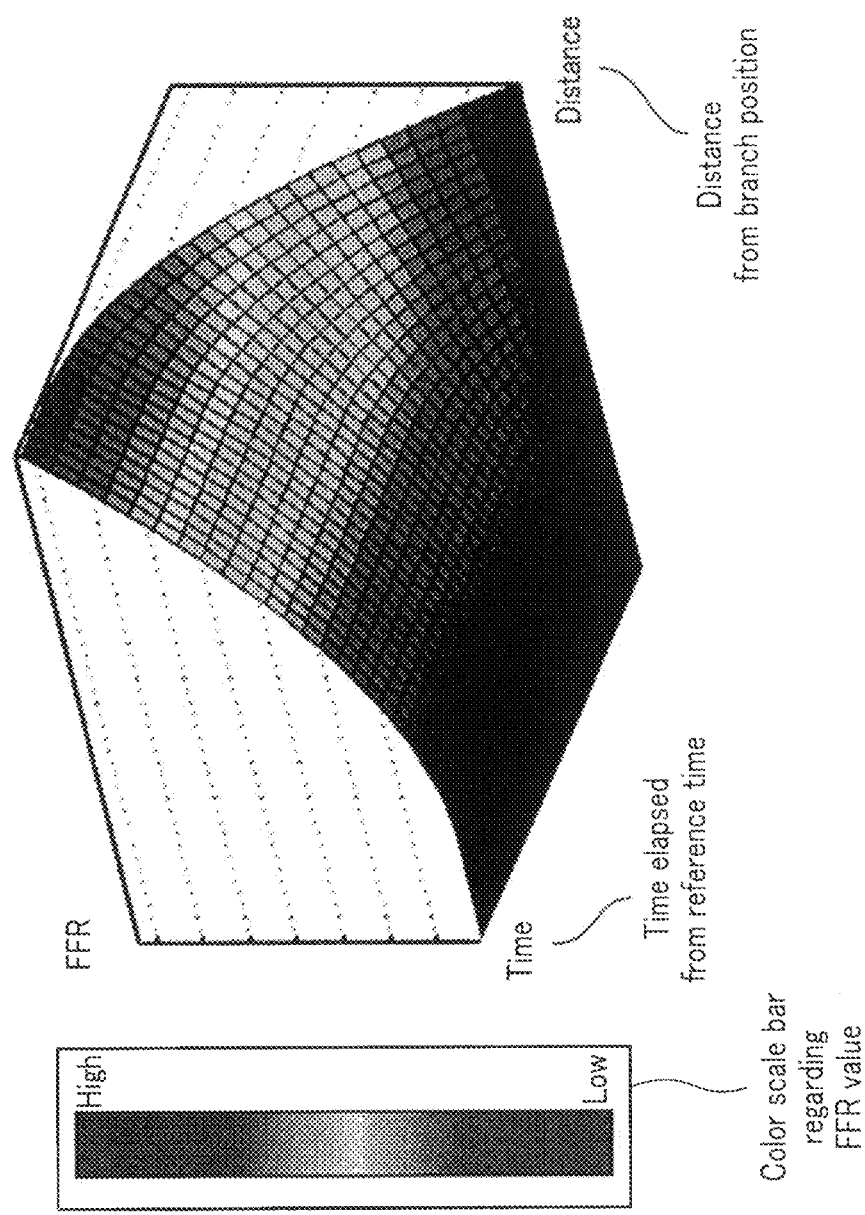
FIG. 8 is a view showing an example of a 3D graph in the blood vessel display mode.

FIG. 8 is a view showing an example of a 3D graph. As shown in FIG. 8, the 3D graph may be a color graph in accordance with the FFR value. At this time, an LUT used for the color graph display is, for example, the first LUT. This LUT may be an LUT generated by the LUT generation circuitry 13 based on an FFR value included in a blood vessel portion to be displayed. A color scale bar regarding the FFR value represents color information corresponding to the FFR value based on an LUT used for the color graph. In the blood vessel display mode, the 3D graph suffices to be a graph from which the user can easily interpret the time in pulsation, a position at a blood vessel portion to be displayed, and the magnitude of the FFR value. This graph may be, for example, a 2D color map obtained by converting, by the color map conversion circuitry 14 in accordance with the first LUT, a 2D map defined by two axes that are the lapse of time and a distance from a branch position.

(FFR Value-Limited Mode)

The FFR value-limited mode is a mode in which a temporal change of a superposed image in a specific FFR value range in the coronary artery of an object is displayed.

Figure 9:
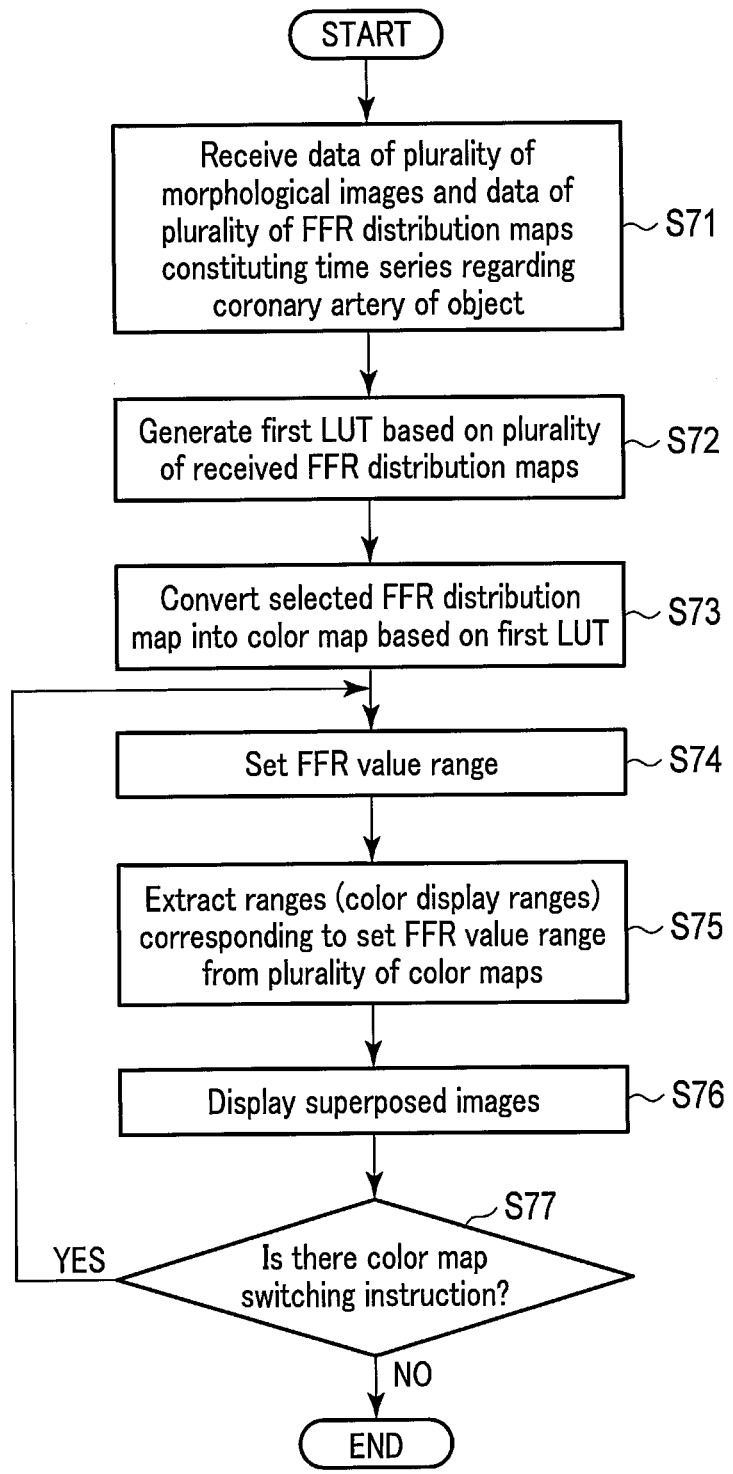
FIG. 9 is a flowchart showing processing procedures in the FFR value-limited mode of the medical image diagnostic apparatus according to this embodiment.

FIG. 9 is a flowchart showing processing procedures in the FFR value-limited mode of the medical image diagnostic apparatus 1 according to this embodiment. First, data of a plurality of morphological images and data of a plurality of FFR distribution maps regarding the coronary artery of an object are received from external apparatuses via the communication interface circuitry 11 (step S71). The LUT generation circuitry 13 generates the first LUT based on the plurality of received FFR distribution maps (step S72).

Based on the first LUT, the color map conversion circuitry 14 converts the plurality of FFR distribution maps into a plurality of corresponding first color maps, respectively (step S73).

An input of an FFR value range for setting a color display range is accepted in accordance with a user instruction via the input circuitry 16 (step S74).

The display range setting circuitry 18 extracts, from a plurality of color maps, ranges corresponding to the FFR value range set in step S74 (or step S77) (step S75). The extracted range serves as a color display range.

The display 20 sets the color display range as a display target, and displays superposed images obtained by superposing a plurality of color maps and a plurality of morphological images respectively corresponding in phase to the plurality of color maps (step S76).

If the user changes the FFR value range, the process shifts to step S75 (step S77).

Note that the specific period display mode and the thinning display mode out of the plurality of display modes described above are modes in which a superposed image to be displayed is limited. The local display mode and the FFR value-limited mode are modes in which the range where an image is displayed in the color of a color map displayed over a morphological image is limited. These modes are not only singly used, and a display in a combination of these modes is possible. For example, when the specific period display mode and the FFR value-limited mode are combined, a superposed image corresponding to a specific period complying with a user instruction is displayed, and the color display range of a superposed color map is limited.

The medical image diagnostic apparatus 1 having the above-described display modes according to this embodiment can obtain the following effects.

In the specific period display mode, the medical image diagnostic apparatus 1 according to this embodiment can display a temporal change of the FFR result of a coronary artery that is limited to a specific period in one cycle of heart beats. In the thinning processing mode, the medical image diagnostic apparatus 1 according to this embodiment can display a temporal change of the FFR result of the coronary artery in a state in which variations of the FFR value per unit time are decreased by adjusting the thinning ratio. In the local display mode, only an area of user's interest (angiostenosis position, blood vessel branch position, and range of a blood vessel having a predetermined width or more) is displayed in a color corresponding to the magnitude of the FFR value. To the contrary, an area of no interest excluding the area of interest is not displayed in color, and a morphological image is displayed directly. Hence, the user can interpret a temporal change of the FFR result regarding the area of interest of the coronary artery. In the blood vessel display mode, the medical image diagnostic apparatus 1 according to this embodiment can display a temporal change of the FFR result of each blood vessel. In the FFR value-limited mode, only a range corresponding to a set FFR value range is displayed in a color corresponding to the magnitude of the FFR value. In a range excluding the set FFR value range, a morphological image is directly displayed. Thus, the user can interpret a temporal change of the FFR result regarding an area corresponding to an FFR value range of interest. For the purpose of conversion from an FFR distribution map into a color map, an LUT registered in advance may be used, or another LUT generated based on an FFR value included in the color map of a display target as described above may be used. The LUT and the other LUT have different FFR value ranges included in a correspondence table. For example, the upper limit value of the FFR value is 1 and its lower limit value is 0.2 in the LUT, whereas the upper limit value of the FFR value is 1 and its lower limit value is 0.7 or the like in the other LUT. The use of the other LUT makes it easy to see the distribution of FFR values on the color map of a display target.

Each of the plurality of display modes and display methods described above is a display mode corresponding to one of three types of limitations: the limitation of the number of superposed images to be displayed; the limitation of a range to be displayed; and the limitation of a range to be displayed in color. These limitations aim to make it easy to see a temporal change of the FFR result of a coronary artery that changes quickly. The medical image diagnostic apparatus 1 having the above-described display modes according to this embodiment can improve the image interpretation efficiency of a user on a display regarding a temporal change of the FFR result.

(Modification)

A medical image diagnostic apparatus 1 according to a modification of this embodiment will be explained with a focus on a difference from the medical image diagnostic apparatus 1 according to this embodiment.

Figure 10:
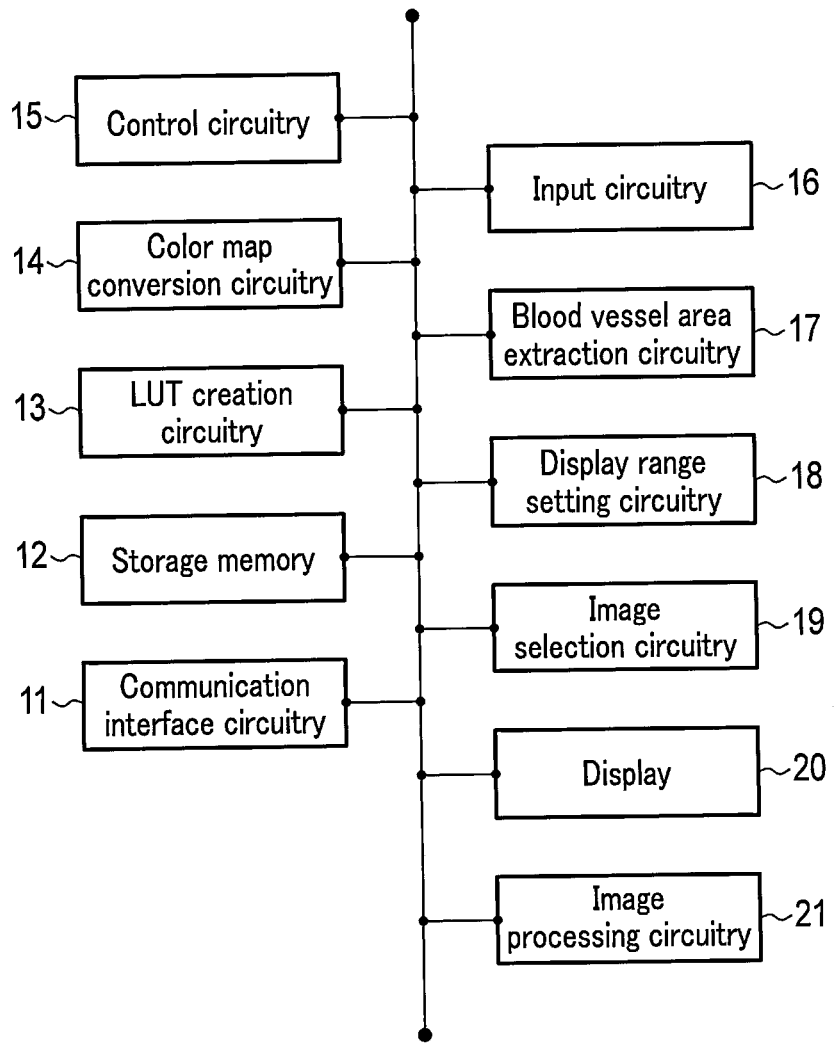
FIG. 10 is a block diagram showing an example of the arrangement of a medical image diagnostic apparatus according to a modification of this embodiment.

FIG. 10 is a block diagram showing an example of the arrangement of the medical image diagnostic apparatus 1 according to the modification of this embodiment. As shown in FIG. 10, the difference from the medical image diagnostic apparatus 1 according to this embodiment is that an image processing circuitry 21 is added to the building components.

The storage memory 12 stores a plurality of volume data constituting a time series regarding a cardiac muscle to which the coronary artery of an object supplies blood. The volume data are collected by a CT apparatus, an MRI apparatus, a SPECT apparatus, a PET apparatus, and the like.

The image processing circuitry 21 is processing circuitry that generates a plurality of functional images respectively corresponding in phase to a plurality of superposed images based on the plurality of volume data stored in the storage memory 12. The image processing circuitry 21 reads a program corresponding to an image processing function from storage memory 12, and executes the program to realize the image processing function. Functional images are, for example, a myocardial perfusion image and a polar map.

The display 20 performs position matching of a plurality of superposed images obtained by superposing a plurality of color maps and a plurality of morphological images respectively corresponding in phase to the plurality of color maps, and displays them over a plurality of functional images respectively corresponding in phase to the superposed images. Note that FIG. 5 shows a display example using a myocardial perfusion as a functional image, and FIG. 6 shows a display example using a polar map as a functional image.

In the medical image diagnostic apparatus 1 according to this embodiment, the storage memory 12 stores in advance data of functional images, for example, data of a myocardial perfusion image and data of a polar map. To the contrary, in the medical image diagnostic apparatus 1 according to the modification of this embodiment, the storage memory 12 stores a plurality of volume data constituting a time series regarding a cardiac muscle to which the coronary artery of an object supplies blood. The image processing circuitry 21 can appropriately generate functional images, for example, a myocardial perfusion image and polar map in accordance with a user instruction. When the display 20 displays a superposed image over a functional image, the medical image diagnostic apparatus 1 according to this modification can improve the degree of freedom of display much more than in the medical image diagnostic apparatus 1 according to this embodiment.

The above described "processing circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Note that programs may be directly incorporated in processing circuitry instead that programs are stored in storage memory 12. In this case, the processing circuitry reads programs incorporated in circuitry and executes the programs to realizes predetermined functions.

Each function (each component) in the present embodiment is not necessary to be corresponded to a single processing circuit and may be realized by a plurality of processing circuits. To the contrary, for example, at least two functions (at least two components) may be realized by a single processing circuit. Further, a plurality of functions (a plurality of components) may be realized by a single processing circuit.

While the embodiment of the inventions has been described, the embodiment has been presented by way of an example only, and is not intended to limit the scope of the inventions. Indeed, the embodiment may be embodied in a variety of other forms; furthermore, various omissions, substitutions and changes may be made without departing from the spirit of the inventions. The appended claims and their equivalents are intended to cover such forms or modifications as would fall within the scope and spirit of the inventions. For example, the processing regarding switching of the color map, which is included in the flowcharts shown in FIGS. 2, 3, and 9, can be omitted. In the embodiment and the modification of the embodiment, a target (range) to be displayed in color on a color map is automatically limited based on an FFR value, an angiostenosis position, a blood vessel branch position, and the area of a blood vessel having a predetermined width or more, and a superposed image to be displayed is automatically limited from a plurality of superposed images based on the heart beat phase. However, a target to be converted into a color map may be limited by the same method. These embodiments and their modifications are incorporated in the scope and sprit of the present invention, and are also incorporated in the scope of the invention and its equivalents defined in the appended claims.

The invention claimed is:

1. A medical image diagnostic apparatus comprising:
a storage memory configured to store data of a plurality of Fractional Flow Reserve (FFR) distribution maps constituting a time series regarding a coronary artery, and data of a plurality of morphological images corresponding to the time series;
processing circuitry configured to convert the plurality of FFR distribution maps into a plurality of corresponding color maps, respectively; and
a display configured to display a plurality of superposed images obtained by superposing the plurality of color maps and the plurality of morphological images respectively corresponding in phase to the plurality of color maps,
wherein the display restricts display targets for the plurality of color maps based on the plurality of FFR distribution maps or the plurality of morphological images.

2. The medical image diagnostic apparatus according to claim 1, wherein the display sets, as display targets, ranges respectively specified from the plurality of FFR distribution maps based on an FFR value, and displays a plurality of superposed images obtained by superposing the plurality of color maps and the plurality of morphological images respectively corresponding in phase to the plurality of color maps.

3. The medical image diagnostic apparatus according to claim 1, wherein the processing circuitry specifies, respectively from the plurality of morphological images, at least one of an angiostenosis position of the coronary artery, a blood vessel branch position, and a position of a blood vessel having not less than a predetermined width, and
the display sets, as display targets, ranges respectively specified from the plurality of color maps based on at least one of the angiostenosis position, the blood vessel branch position, and the position of the blood vessel having not less than the predetermined width, and displays a plurality of superposed images obtained by superposing the plurality of color maps and the plurality of morphological images respectively corresponding in phase to the plurality of color maps.

4. The medical image diagnostic apparatus according to claim 1, wherein
the time series includes at least one cycle of heart beats, and
the display sets, as display targets, a plurality of color maps extracted from the plurality of color maps based on a heart beat phase, and displays at least two superposed images obtained by superposing the plurality of color maps and the at least two morphological images respectively corresponding in phase to the at least two color maps.

5. The medical image diagnostic apparatus according to claim 1, wherein the processing circuitry generates data of a correspondence table that associates data of a plurality of colors respectively with a plurality of FFR values defined by upper limit values and lower limit values of FFR values included in the plurality of FFR distribution maps, and
the processing circuitry converts the plurality of FFR distribution maps into a plurality of corresponding color maps based on the correspondence table, respectively.

6. The medical image diagnostic apparatus according to claim 1, wherein the processing circuitry generates data of another correspondence table that associates data of a plurality of colors respectively with a plurality of FFR values defined by upper limit values and lower limit values of FFR values included in display targets for the plurality of color maps, and
the processing circuitry converts the plurality of FFR distribution maps into a plurality of corresponding color maps based on the correspondence table, respectively.

7. The medical image diagnostic apparatus according claim 1, wherein the processing circuitry generates data of a correspondence table that associates data of a plurality of colors respectively with a plurality of FFR values defined by upper limit values and lower limit values of FFR values included in the plurality of FFR distribution maps, and data of another correspondence table that associates data of a plurality of colors respectively with a plurality of FFR values defined by upper limit values and lower limit values of FFR values included in display targets for the plurality of color maps, and the display switches, in accordance with a user instruction, color maps to be displayed over the plurality of morphological images, out of a plurality of color maps generated based on the correspondence table and a plurality of color maps generated based on the other correspondence table.

8. The medical image diagnostic apparatus according to claim 1, wherein the storage memory stores a plurality of volume data constituting a time series regarding a cardiac muscle to which the coronary artery supplies blood, the processing circuitry generates, based on the plurality of volume data, a plurality of functional images constituting the time series regarding the cardiac muscle, and the display displays the plurality of superposed images on the plurality of corresponding functional images by position matching, respectively.

9. The medical image diagnostic apparatus according to claim 8, wherein the functional image includes a myocardial perfusion image or a polar map.

10. The medical image diagnostic apparatus according to claim 1, wherein the storage memory stores data of a plurality of functional images constituting a time series regarding a cardiac muscle to which the coronary artery supplies blood, and the display displays the plurality of superposed images on the plurality of corresponding functional images by position matching, respectively.

11. The medical image diagnostic apparatus according to claim 10, wherein the functional image includes a myocardial perfusion image or a polar map.

12. The medical image diagnostic apparatus according to claim 3, wherein the processing circuitry divides the coronary artery into a plurality of blood vessel portions based on a specified blood vessel branch position, and as for one blood vessel portion out of the plurality of blood vessel portions, the display displays a graph defined by three axes that are a distance from the blood vessel branch position serving as a start point, a time from predetermined time of the time series serving as a start point, and an FFR value corresponding to the distance from the blood vessel branch position serving as the start point and the time from the predetermined time of the time series serving as the start point.

* * * * *